United States Patent
Hewitt et al.

(10) Patent No.: US 11,623,220 B2
(45) Date of Patent: Apr. 11, 2023

(54) DEVICE FOR STORING AND TRANSPORTING TISSUE SPECIMENS

(71) Applicant: THE USA, AS REPRESENTED BY THE SECRETARY, DEPARTMENT OF HEALTH & HUMAN SERVICES, Bethesda, MD (US)

(72) Inventors: Stephen M. Hewitt, Bethesda, MD (US); Robert A. Star, Bethesda, MD (US); Jeffrey C. Hanson, Bethesda, MD (US); Hiroshi Kojima, Bethesda, MD (US); Russell Bandle, Bethesda, MD (US); Armando Filie, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 731 days.

(21) Appl. No.: 16/606,555

(22) PCT Filed: Apr. 26, 2018

(86) PCT No.: PCT/US2018/029623
§ 371 (c)(1),
(2) Date: Oct. 18, 2019

(87) PCT Pub. No.: WO2018/200853
PCT Pub. Date: Nov. 1, 2018

(65) Prior Publication Data
US 2021/0094029 A1   Apr. 1, 2021

Related U.S. Application Data

(60) Provisional application No. 62/490,415, filed on Apr. 26, 2017.

(51) Int. Cl.
*B01L 3/00* (2006.01)
*G01N 35/10* (2006.01)
(Continued)

(52) U.S. Cl.
CPC .......... *B01L 3/508* (2013.01); *A61B 10/0096* (2013.01); *A61B 10/0233* (2013.01);
(Continued)

(58) Field of Classification Search
CPC ................. B01L 3/508; B01L 2200/18; B01L 2300/042; B01L 2300/0803;
(Continued)

(56) References Cited

FOREIGN PATENT DOCUMENTS

WO   WO 2009/136445   11/2009
WO   WO-2009136445 A1 *  11/2009   ......... A61B 10/0038
(Continued)

OTHER PUBLICATIONS

International Search Report & Written Opinion issued for International Application No. PCT/US2018/029623 dated Sep. 27, 2018.

*Primary Examiner* — Jennifer Wecker
*Assistant Examiner* — Oyeleye Alexander Alabi
(74) *Attorney, Agent, or Firm* — Klarquist Sparkman, LLP

(57) ABSTRACT

A container comprising:
a first panel;
a second panel opposing the first panel;
a first side;
a second side opposing the first side;
a third side;
a fourth side opposing the third side;
wherein each of the sides joins the first panel and the second panel;
a chamber defined by the four sides, the first panel, and the second panel, wherein the chamber is configured to receive a biological specimen;

(Continued)

a port defined in the first side;
a plug inserted into the port;
an opening defined in the second side; and
a closure element coupled to the opening,
wherein the chamber is leak proof.

33 Claims, 14 Drawing Sheets

(51) Int. Cl.
  *A61B 10/00* (2006.01)
  *A61B 10/02* (2006.01)
(52) U.S. Cl.
  CPC ..... *B01L 2200/18* (2013.01); *B01L 2300/042* (2013.01); *B01L 2300/0803* (2013.01); *B01L 2300/0809* (2013.01)
(58) Field of Classification Search
  CPC ........... B01L 2300/0809; B01L 3/5082; A61B 10/0096; A61B 10/0233; G01N 2001/315
  See application file for complete search history.

(56) References Cited

FOREIGN PATENT DOCUMENTS

| | | | |
|---|---|---|---|
| WO | WO 2013/142393 | 9/2013 | |
| WO | WO-2013142393 A1 * | 9/2013 | ........... A01N 1/0247 |

* cited by examiner

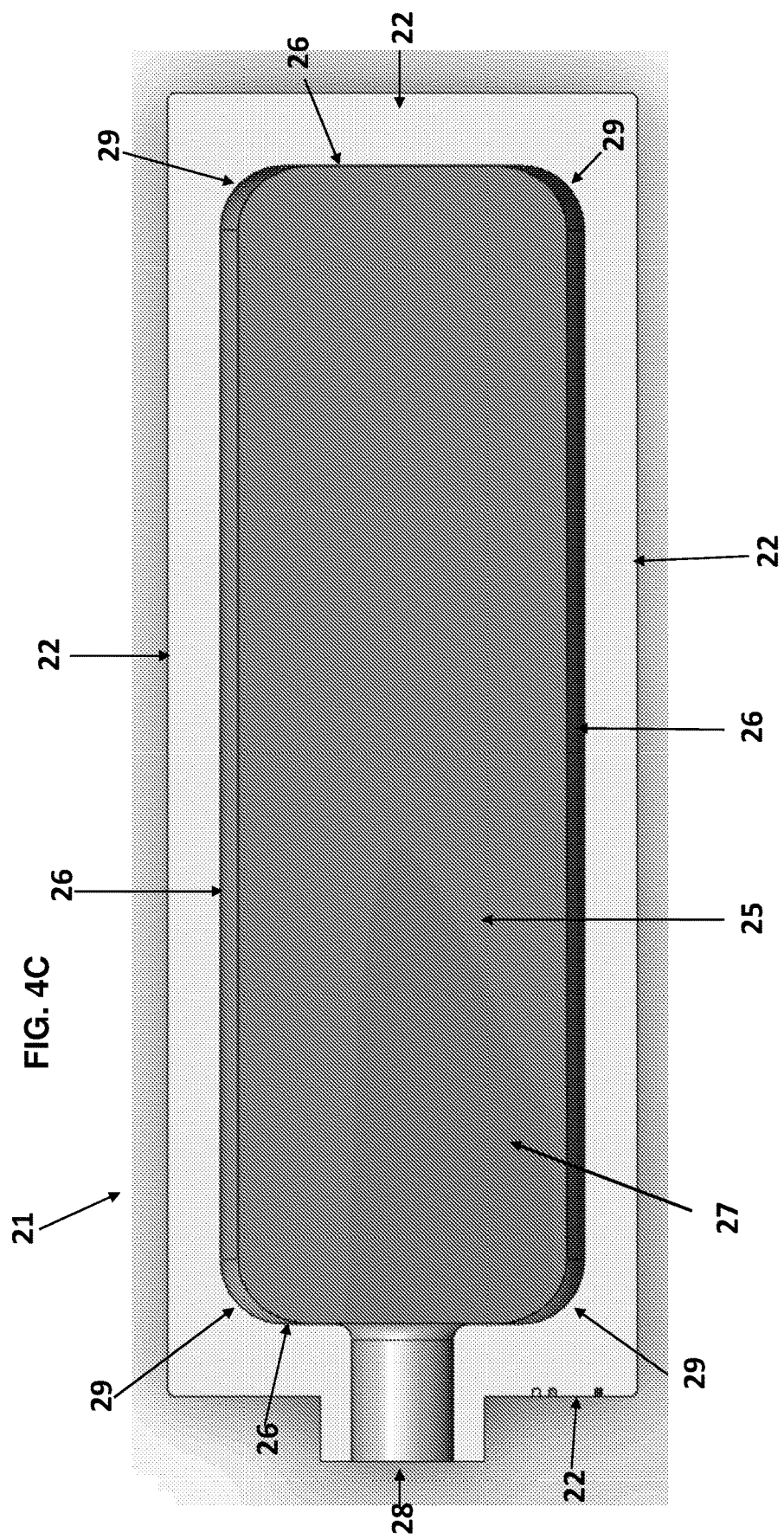

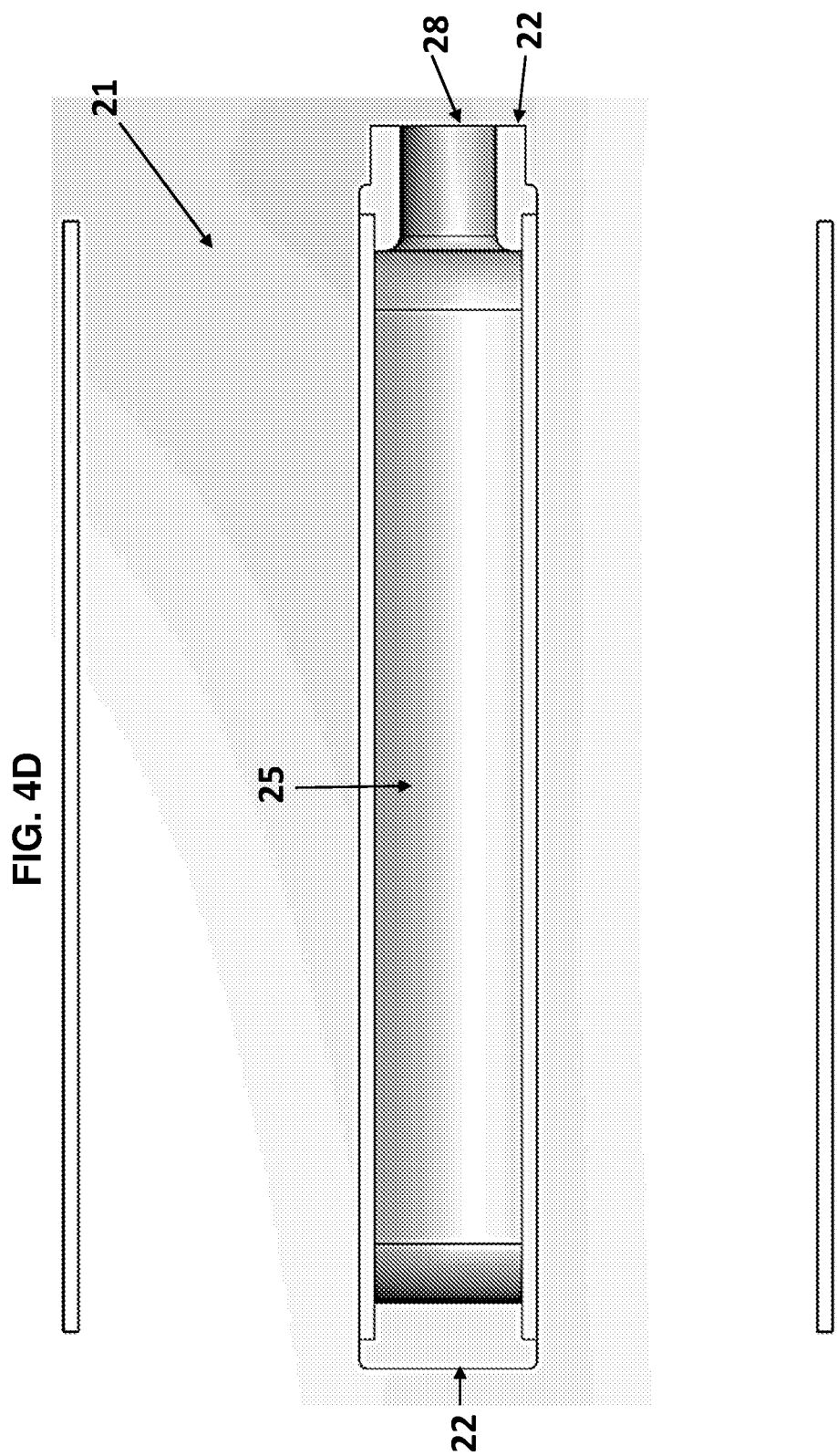

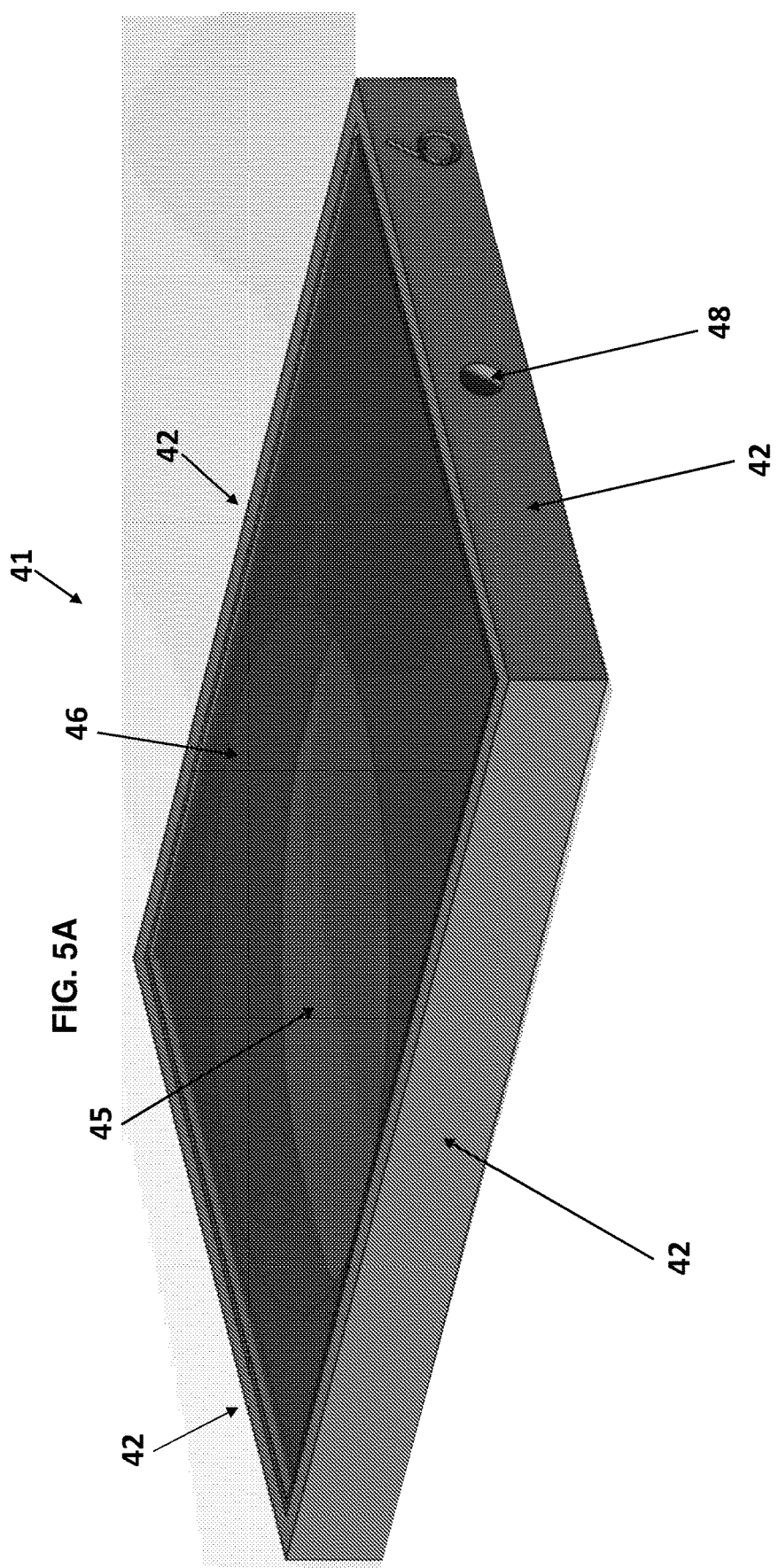

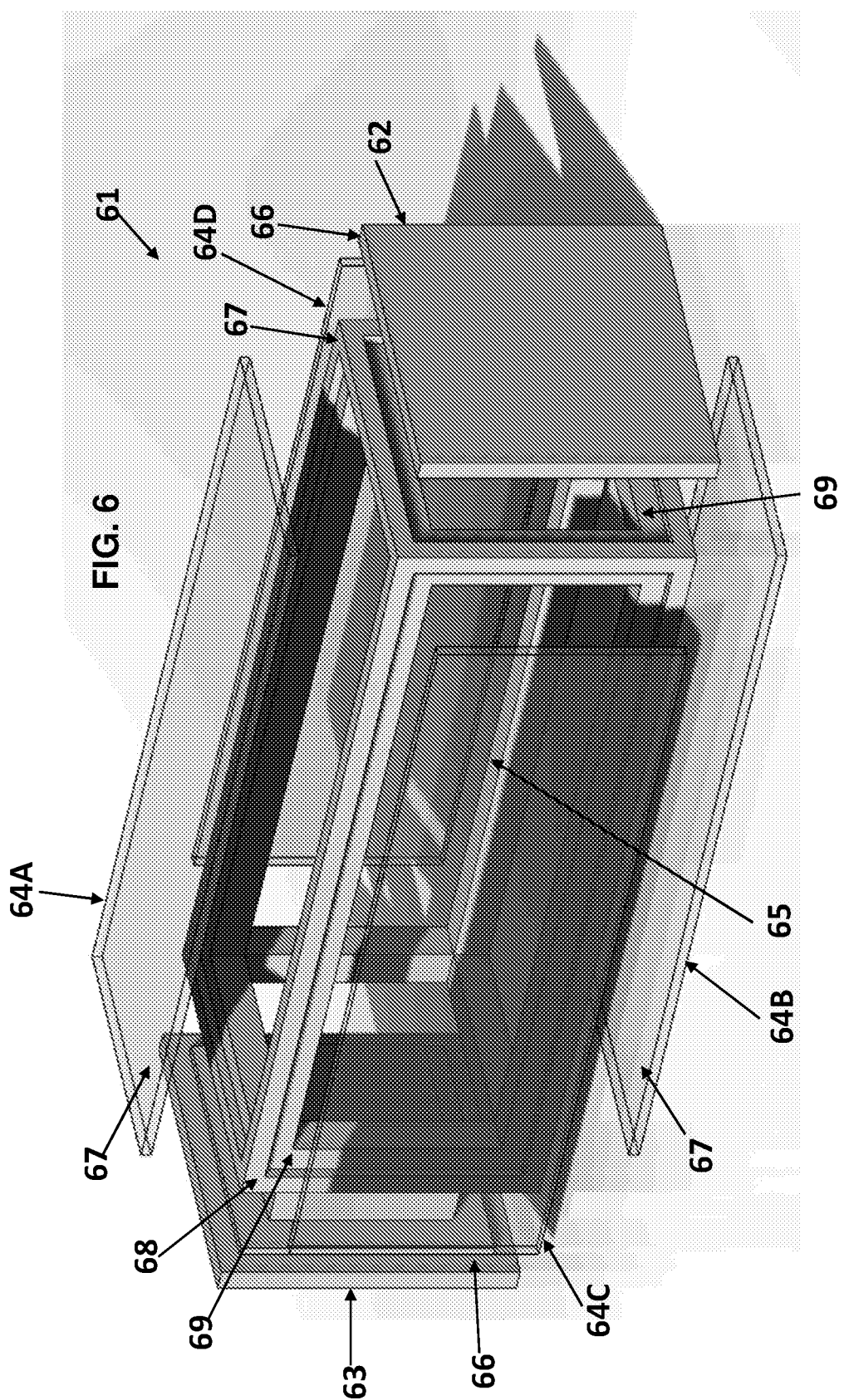

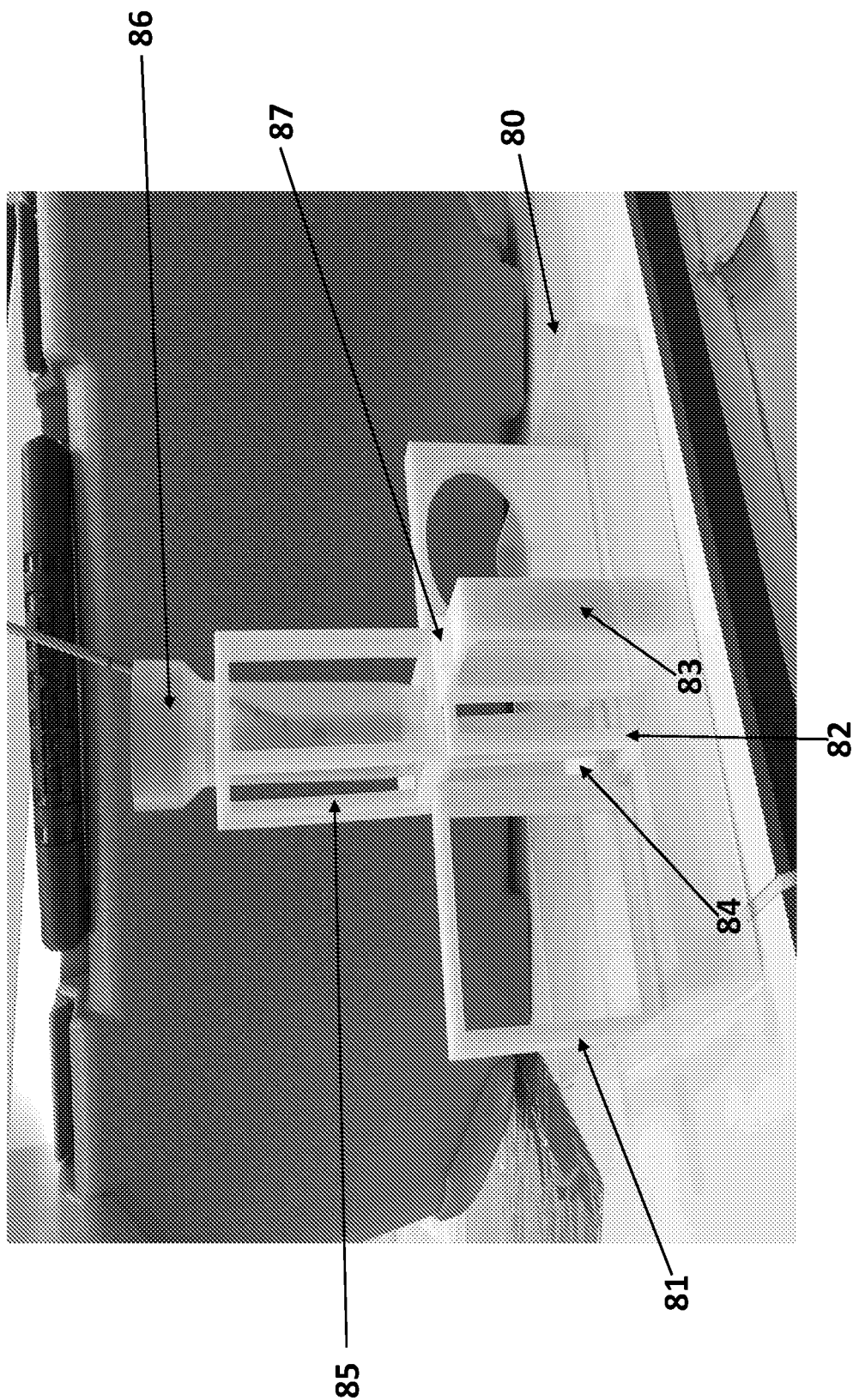

DEVICE FOR STORING AND TRANSPORTING TISSUE SPECIMENS

This is the U.S. National Stage of International Application No. PCT/US2018/029623, filed Apr. 26, 2018, which was published in English under PCT Article 21(2), which application in turn claims the benefit of U.S. Provisional Application No. 62/490,415, filed Apr. 26, 2017, which is incorporated herein by reference in its entirety.

BACKGROUND

Currently, there are commercially available tubes for the collection of blood or containers for the collection of other body fluids or tissue. The "vacutainer" is the only unit that is pre-filled with specified preservatives, with a partial vacuum to facilitate drawing the fluid into the container. However the vacutainer container is used only for body fluid collection with syringes and/or needles and is not suitable for the collection of tissue. Current cups and containers for tissue specimen collection are simple enclosures that are not filled with any particular solution. Solution may be added by a user and it not only takes time to do that but also introduces variability (differences will be seen from one collection site to the other in type and volume of a solution used). When specimen is collected with the purpose of keeping it alive in a defined environment while transporting to the site of analysis, the most common challenge today is sterility. Maintaining the sterility of a tissue specimen is not ensure by current collection methods, in which the tissue is exposed to the atmosphere, in the absence of a sterile or controlled airflow environment. Specimens collected for evaluation of infectious agents, microbiome, or culturing (propagation) of cells may be negatively impacted by the current handling protocols, with exposure to non-sterile environments and instruments. The only methods that are currently available for examination of an unperturbed biopsy specimen (such as biopsies of the kidney or liver for diagnosis of diseases of these organs) under a microscope, require manipulation of this tissue (such as placing it on the gauze and picking it up with forceps) that can damage tissue and jeopardize tissue morphology and takes time during which degradation of biologically important biomolecules may occur.

SUMMARY

Disclosed herein is a container comprising:
a first panel;
a second panel opposing the first panel;
a first side;
a second side opposing the first side;
a third side;
a fourth side opposing the third side;
wherein each of the sides joins the first panel and the second panel;
a chamber defined by the four sides, the first panel, and the second panel, wherein the chamber is configured to receive a biological specimen;
a port defined in the first side;
a plug inserted into the port;
an opening defined in the second side; and
a closure element coupled to the opening, wherein the chamber is leak proof.

Also disclosed herein is a container in the shape of a rectangular cuboid comprising:
a transparent first panel;
a transparent second panel opposing the first panel;
a first side;
a second side opposing the first side;
a third side;
a fourth side opposing the third side;
wherein each of the sides joins the first panel and the second panel;
a chamber defined by the four sides, the first panel, and the second panel, wherein the chamber is configured to receive a biological specimen;
a port defined in the first side;
an opening defined in the second side; and
a closure element coupled to the opening, wherein the closure element is perforated with at least one hole that communicates with the opening in the second side.

Further disclosed herein is a container comprising:
six sides, wherein at least one of the sides is optically transparent and/or at least one of the sides is removable;
an internal chamber defined by a peripheral side wall and two opposing planar surfaces; and
at least one opening in at least one of the six sides, wherein the opening communicates from exterior of the container into the chamber and wherein the opening is configured to introduce a biological specimen into the chamber.

Additionally disclosed herein is a container comprising:
a transparent elongated first panel having an exterior surface and an interior surface;
a transparent elongated second panel opposing the first panel, wherein the second panel has an exterior surface and an interior surface;
a transparent elongated third panel having an exterior surface and an interior surface;
a transparent elongated fourth panel opposing the third panel, wherein the second panel has an exterior surface and an interior surface;
a first end having an exterior surface and an interior surface;
a second end opposing the first end, the second end having an exterior surface and an interior surface, wherein at least one of the first end and the second end is removable;
a housing coupled to the first panel, the second panel, the third panel, the fourth panel, the first end, and the second end; and
an internal chamber bounded the interior surface of the first panel, the interior surface of the second panel, the interior surface of the third panel, the interior surface of the fourth panel, the interior surface of the first end, and the interior surface of the second end.

Also disclosed herein are methods for collecting and storing a biological specimen, comprising obtaining a biological specimen from a subject and placing the biological specimen in the chamber of a container as disclosed herein.

Further disclosed herein are methods for collecting and storing a tissue sample, comprising obtaining a tissue sample from a subject via biopsy needle and inserting the tissue sample-loaded biopsy needle into the chamber of a container as disclosed herein via the closure element.

The foregoing will become more apparent from the following detailed description, which proceeds with reference to the accompanying figures.

BRIEF DESCRIPTION OF THE DRAWINGS

FIGS. 4A-4D are views of another embodiment of a container that includes a chamber bounded by a curvilinear surface. FIG. 4A is a perspective view; FIG. 4B is an exploded perspective view; FIG. 4C is a cross sectional top view; and FIG. 4D is an exploded cross sectional side view.

FIGS. 5A and 5B are views of another embodiment of a container that includes a chamber bounded by a curvilinear surface. FIG. 5A is a perspective view; and FIG. 5 is an exploded perspective view.

FIG. 6 is an exploded perspective view of a further embodiment of a container.

FIG. 7 is photograph of an illustrative holder for the container.

DETAILED DESCRIPTION

Figure 1:
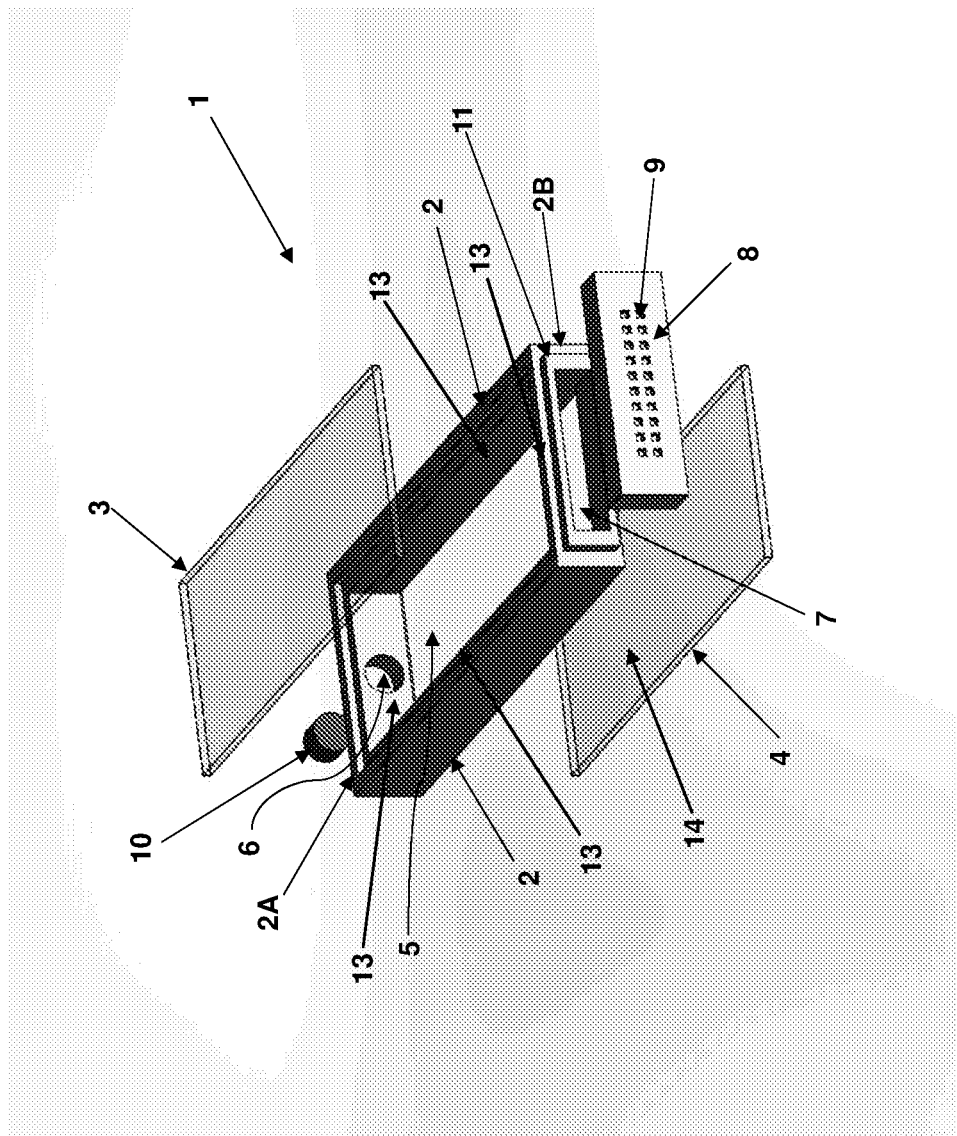
FIG. 1 is a perspective view of an embodiment of a container.
Figure 2A:
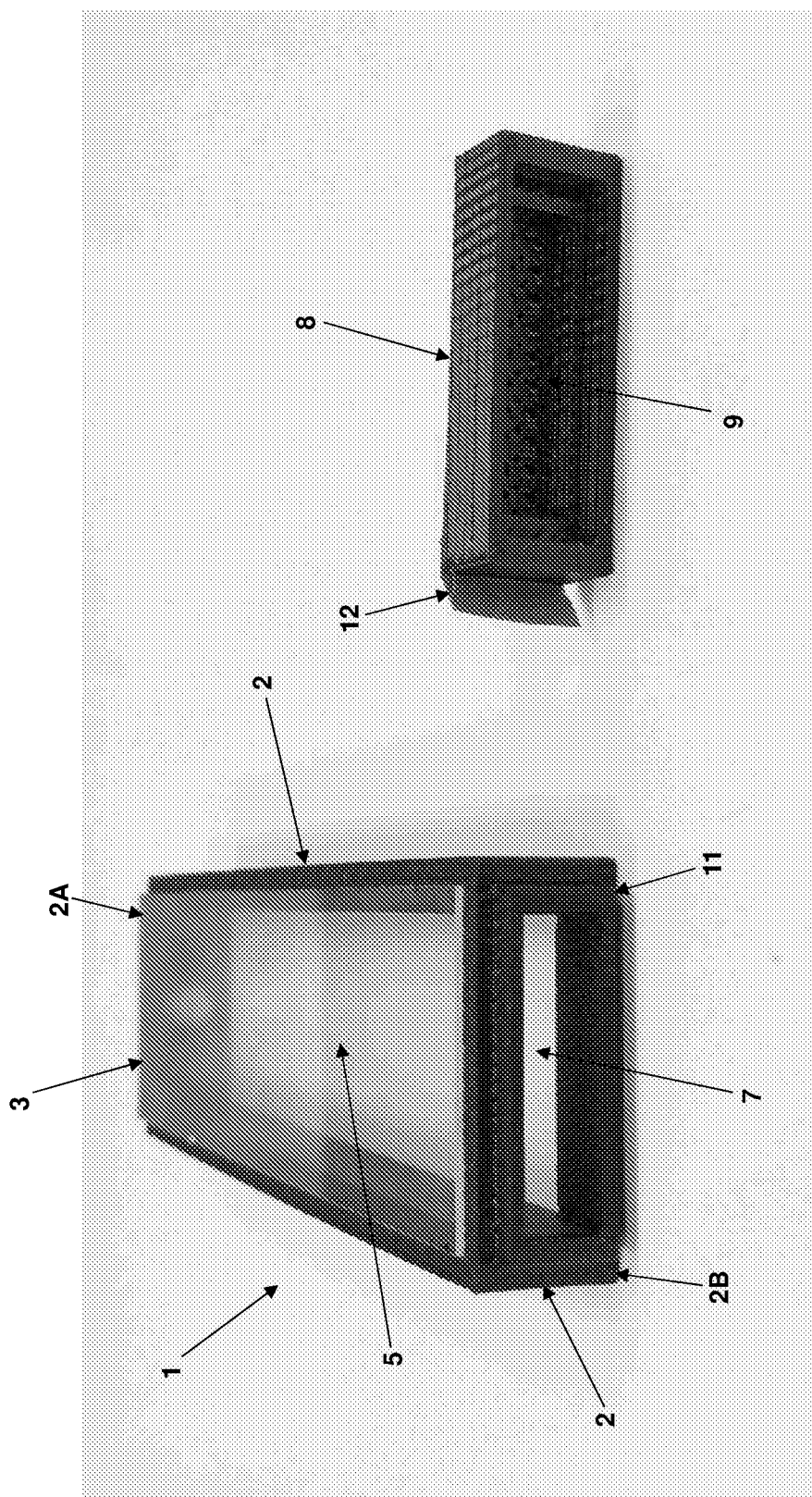
FIGS. 2A-2D are photographs of an embodiment of a container.
Figure 2B:
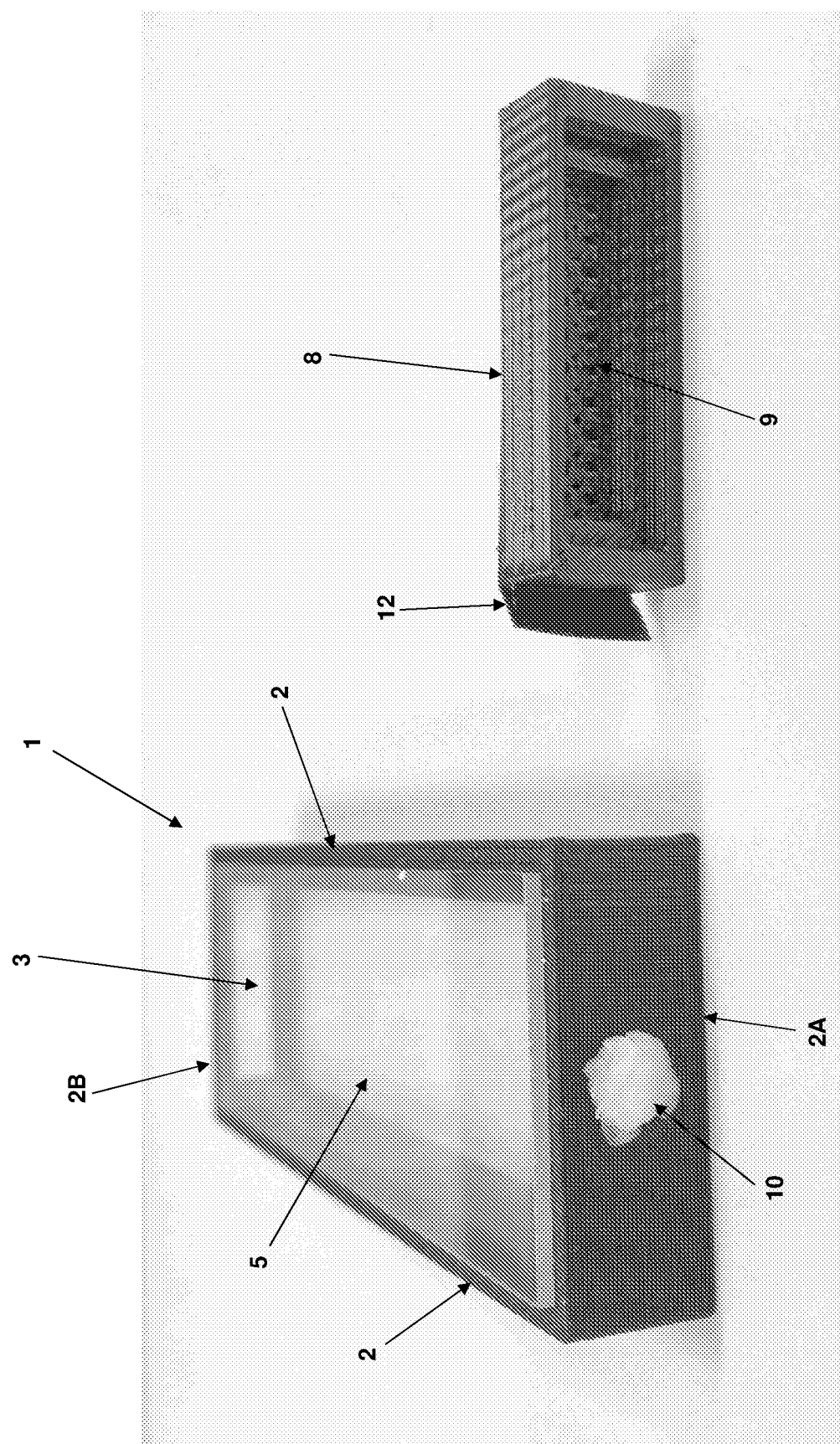
Figure 2C:
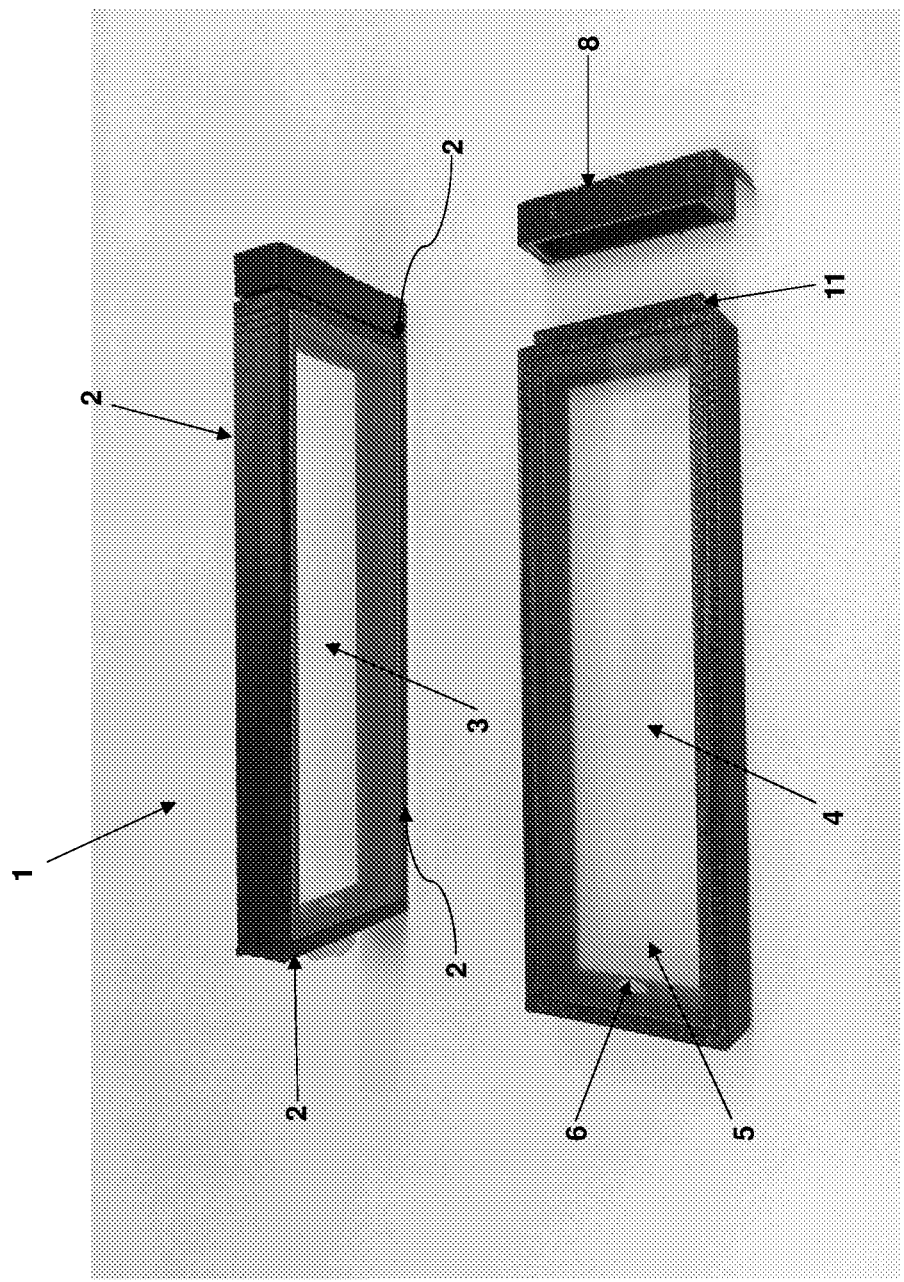
Figure 2D:
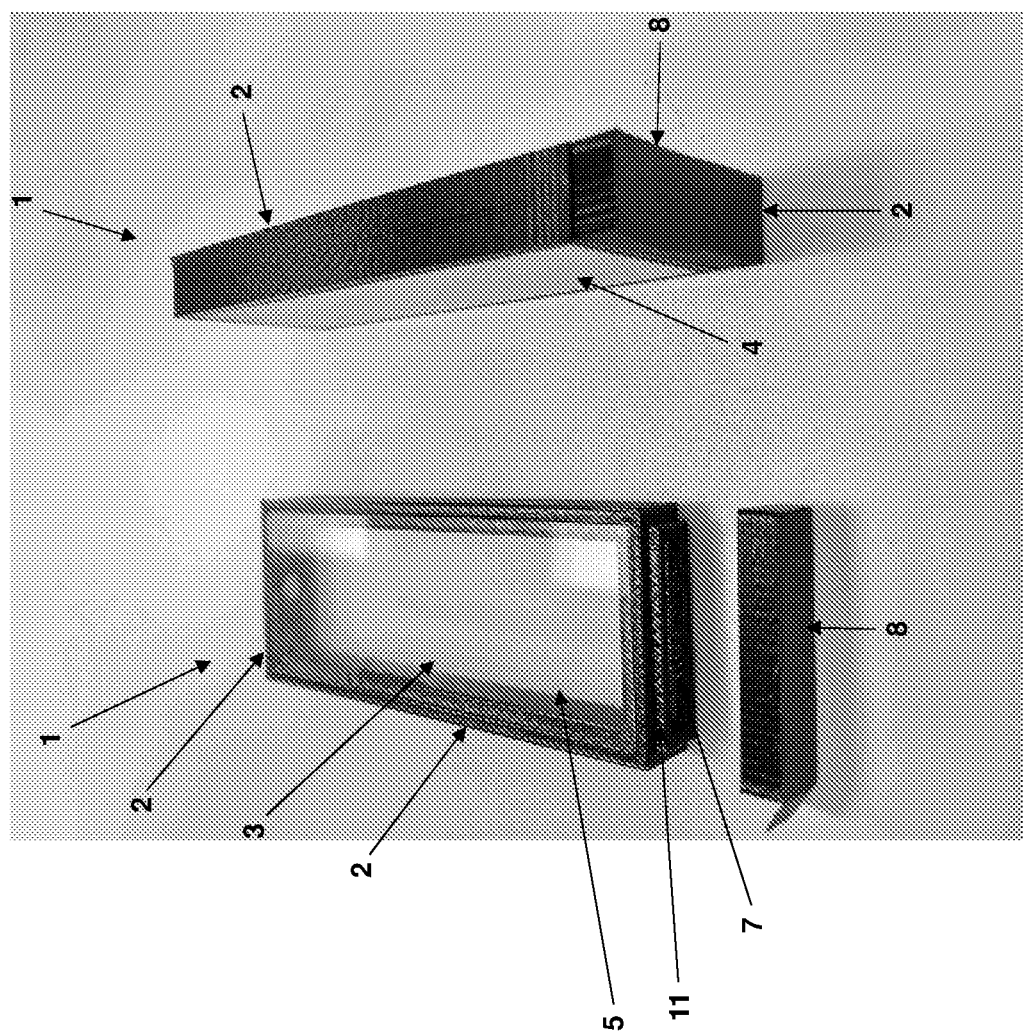

Disclosed herein are containers and methods for storing and transporting tissue samples and cell aspirates, particularly those obtained by means of a needle biopsy, needle aspirate, biopsy forceps or similar approaches. The containers and methods disclosed herein enable cell and tissue sample collection in a controlled fashion and make comparison of data obtained from such collection more reliable. For example, the containers and methods may improve the integrity of the biospecimens (e.g, cells and tissues) for subsequent analysis.

In certain embodiments, the container is rectangular cuboid or box-like in shape and defines at least one chamber configured for holding at least one biological specimen. In certain embodiments, the container has only a single internal chamber. In certain embodiments, the internal chamber may be divided by a partition or membrane as described in more detail below. In certain embodiments, the chamber can be pre-loaded with a liquid and/or gas prior to introduction of the biological specimen. In certain embodiments, the chamber is leak proof thus allowing for storing and/or transporting the specimen in a controlled environment. "Leak proof" as used herein means that once the chamber is sealed there is no fluid (liquid or gas) exchange between the interior of the chamber and the ambient atmosphere outside of the chamber. In some other embodiment, the container may be gas permeable to allow introduction of air to keep the sample alive.

In certain embodiments, the chamber is bounded on all sides by flat surfaces. The certain embodiments, the chamber is quadrilateral-shaped (e.g., square, rectangle (e.g., cuboid), trapezoid).

In certain embodiments, the chamber is bounded by at least one curvilinear surface. In certain embodiments, the chamber is bounded by flat surfaces and curvilinear surfaces. In certain embodiment, the chamber has rounded corner surfaces (e.g., a rounded rectangle, a rounded square, or a truncated circle). In certain embodiments, the chamber is cylindrical, cone-shaped, or disc-shaped.

In certain embodiments, the chamber may have a volume of 1 to 50 $cm^3$. This volume range enables a 1:10 tissue: medium (e.g., solution) range of 100 mg to 5 grams and a 1:20 tissue:medium (e.g., solution) range of 0.5 mg to 2.5 grams. The container may collect 20 mg to 500 mg of a specimen, the volume of the chamber is sufficient to accommodate a desired medium.

In instances wherein the chamber is filled or expected to be filled with a defined volume or tissue and/or medium that is less than the total volume of the chamber the remainder volume could be occupied by: a vacuum; a defined gas; a combination of a vacuum and a defined gas; or a gel or non-reactive medium (e.g., mineral oil).

In certain embodiments, the chamber may divided by a membrane or partition for separating liquids and/or gases (e.g., mediating dialysis for fluids) or for a scrubber-like activity for a gas. For example, the membrane may be a selectively permeable membrane (e.g., based on a relative difference in buffer or salt concentrations) for exchanging liquids and/or gases. A reactive gas (e.g., sulfur dioxide) could function as a scrubber. Another embodiment is a membrane that is impervious to fluid, but segregates a solid such as activated carbon, and acts a scrubber for gasses that might come off a tissue thus enabling a sealed long term viable cell/tissue device that would regulate $CO_2$ or a similar gas.

In certain embodiments, the container includes four sides, each joined to a first panel and to an opposing second panel. In the rectangular cuboid-shaped containers the first and second panels have an elongated surface area that is greater than the surface area of each of the individual sides. The container also includes at least one specimen port configured for introducing and/or removing a specimen. In certain embodiments, the container has only one port. In certain embodiments, the container has two or more ports. In certain embodiments, the specimen port(s) is located in at least one of the sides of the container. In certain embodiments, one side of the container receives or defines a cap, which may be removable by a user. The cap may be perforated with at least one, and preferably more than one, holes. In other embodiments, the cap that is covering a specimen port or hole is made from a material (e.g., a soft rubber) that a needle can penetrate.

In certain embodiments, all of the panels of the container may be transparent. In certain embodiments, the first and/or second panels of the container may be transparent. In certain embodiments both the first panel and the second panel of the container are optically transparent. The entire panel may be made from a transparent material or the panel may be provided with a transparent window. The transparent panel(s) may enable microscopy (e.g., under a dissection microscope) of the tissue specimen without removal of the specimen from the container. Other embodiments would include optically translucent panels on 4 of 6 sides of a cube to enable transilluminator, reflective illumination as well as side (orthogonal) illumination to enable different forms of observation/imaging with stereoscopes, microscopes and/or advanced optical devices. In certain embodiments, one of the panels is optically transparent and the other opposing panel is opaque (but that allows the passage of light).

In certain embodiments, at least one of the sides of the container may be transparent. The entire side may be made from a transparent material or the side may be provided with a transparent window. The transparent side(s) may enable microscopy or other analysis of the tissue specimen without removal of the specimen from the container. For example, two opposing sides may be transparent to enable side-illumination for lightsheet or fluorescence microscopy. In certain embodiments, all four of the sides may be optically transparent. In certain embodiments, one of the sides is optically transparent and the opposing side is opaque (but that allows the passage of light).

In certain embodiments, at least one of the panels and/or at least one of the sides may be formed of a slide glass (e.g., a slide glass 1.5 mm thick).

In certain embodiments, at least one of the panels and/or at least one of the sides may be formed of coverslip glass (e.g., a coverslip glass 0.1 to 0.5 mm thick).

In certain embodiments, at least one of the panels and/or at least one of the sides may be formed from an inflexible plastic material having a defined refractive index of 1.33 to 1.62.

In certain embodiments, at least one of the panels and/or at least one of the sides may be formed a flexible material (e.g., a thermoplastic). The flexible material may be optically clear or partially opaque). The flexible material may be removable and/or re-sealable.

In certain embodiments, at least one of the panels and/or at least one of the sides is removable and is formed of an optically transparent material.

In certain embodiments, the container may be a molded (e.g., plastic such as injection-molded ABS) single piece design.

The container includes at least one opening into the chamber for introducing and/or removing a desired medium that at least contacts a portion of the tissue specimen. In certain embodiments, the container has only one opening into the chamber for introducing and/or removing a desired medium that at least contacts a portion of the tissue specimen. The medium may be a liquid (e.g., tissue culture medium or fixative) or a gas (like nitrogen, argon, carbon monoxide, sulfur-containing gases (e.g., sulfur dioxide), oxygen, xenon, and/or carbon dioxide) or a combination of a liquid and a gas. The medium may encompass or envelope the tissue specimen. The container may be purchased empty and the medium(s) may be introduced into the chamber by the user of the container, or a chamber with a pre-loaded medium may be provided to the user by the manufacturer. In certain embodiments, the chamber in the container may be filled with a suitable fluid (e.g., a translucent fixative solution or culture medium) for suspending the specimen in the chamber. In another embodiment, liquid medium may be introduced together with partial vacuum. Also, a gel or other semi-solid media (like agar/agarose or hydrogel) can be placed in the chamber, in addition to gas and/or fluids. The gel would hold the specimen in a fixed position and prevent motion. Optimally the gel would be sufficiently translucent to allow imaging.

In certain embodiments the container may only include one opening into chamber that can function both as a port for introducing (and removing, if desired) a specimen and as an opening for introducing (and removing, if desired) a medium that at least contacts a portion of the tissue specimen.

In certain embodiments, the opening into the container may be provided by at least one lid provided in a side and/or panel of the container. The lid may be secured via a gasket.

In certain embodiments, the opening into the chamber may be provided by removing a side or panel of the container.

In some other embodiments, container may have only one port and one filtered end. In some others, it may have a multiplicity of ports on different sides, with or without filters.

Ports may be adapted to luer locks and similar existing and commercially available joiners.

Once the specimen contacts the medium within the chamber, the specimen is processed as desired (e.g., preservation, growth, analysis and/or imaging). After the specimen is processed, the specimen and/or medium may be removed from the chamber, and the container discarded or washed and reused.

For example, the chamber may include a fluid suitable for preservation/fixation rendering the specimen stable and unaltered during transport of the specimen-holding container. In another embodiment, the chamber may include a fluid suitable for preserving a live specimen such as media to maintain cells (e.g., eukaryote/human) alive for culture (e.g., with or without antibiotics). In a further embodiment, the chamber may include culture media for microbiology studies including aerobic or anaerobic environments (including microbiome studies). In a further embodiment, the fluid can include a non-destructive staining fluid for pathologic features (for example, cells and/or extracellular matrix).

Illustrative media include neutral buffered formaldehyde, water, saline, cell culture media, alcohols or organics, glycerol, mineral oil, proteolytic inhibitors, RNA degradation inhibitors (e.g., ammonium salts), glycols, acids (e.g., acetic acid, citric acid, formic acid, oxalic acid), argon-enriched atmosphere in contact with Formalin-Fixation Paraffin Embedding (FFPE) reagents as described in US20150216161, fixatives as described in WO 2017/083729 (e.g., a fixative comprising ethanol, a buffer, glycerol, and acetic acid), transport media (e.g, solutions available from Organ Recovery Systems), and Michel's Transport Fluid.

Each specific chamber/use may be assigned a unique code, for example, a different color (red top, purple top, etc.). The purpose of the color coding is to quickly and reliably identify the use of the chamber (type of fixative, fixative vs. media etc.). Containers could also have an RFID tag and/or bar code embedded for tracking and subject identification purposes, as well as potential recording of desired variables (collection time and date, environmental factors, etc.) The container may include a direct ink, adhesive, or bar code label on a panel or a side. The container may be stabilized on a stand to allow for easier sample introduction or transportation.

In certain embodiments, the dimensions of the container may be designed to hold at least one biopsy tissue specimen. For example, in one embodiment the container may be 1.00×3.00×0.25 inches, for the entire object, with an internal volume on the order of 3 cc. with dimensions being 0.75× 2.5×0.2 inches. In certain embodiments, the container may have outer dimensions of 2.5 cm to 5 cm width, and/or 4 cm to 8 cm length, and/or 2.5 cm to 4 cm thickness (i.e., height). In certain embodiments, the container can be reused multiple times. In certain embodiments, container can be made to be affordable and used only once.

Individual container units may be bundled into a carrier (e.g., a plastic ring carrier that surrounds each container or a box carrier that includes slots for each container). For example, prostate biopsies routinely take 6, 12 and multiples thereof, samples from a single patient with each individual processed with the same reagent. A single carrier that holds 6, 12 or a multiple thereof provides a convenient method for controlling samples from a single patient. In other instances, samples (e.g., 2, 3 or 4) from a single patient may be subjected to different processes.

Illustrative embodiments are shown in FIGS. 1, 2A-2D and 3. The container 1 includes four sides 2, each of which joins a first panel 3 and a second panel 4. In certain embodiments, the four sides 2 together form a housing onto which the first and second panels 3,4 may be coupled. In certain embodiments, the first and second panels 3,4 may be removably coupled to the housing. At least one of the first or second panels 3,4 may be at least partially transparent. In the embodiments shown in FIGS. 1 and 2A-2D both first panel 3 and second panel 4 are entirely made from a transparent material (e.g., glass or plastic). The sides 2, first panel 3 and second panel 4 define a chamber 5. As described above, the chamber 5 is configured for receiving and retaining a specimen. Chamber 5 is defined by four peripheral side wall surfaces 13 and two peripheral panel surfaces 14. Each surface 13,14 is planar. The four peripheral side wall surfaces 13 are also the interior facing surfaces of the four sides 2A-2D, respectively. The two peripheral panel surfaces 14 are also the interior facing surfaces of the first panel 3 and second panel 4, respectively. The chamber 5 is rectangular in top view cross sectional shape, but could be other shapes such as a square.

The container includes a first side 2A and an opposing second side 2B. In certain embodiments, the first side 2A and the second side 2B are shorter in the horizontal direction relative to the other two sides. In the other words, the other two sides are more elongated relative to first side 2A and second side 2B. The first side 2A defines a port 6 communicating directly from the exterior of the container into the chamber 5. In certain embodiments, the port 6 may be a removable cap or a Luer lock, with or without stop cocks. In certain embodiments, a specimen can be introduced into chamber 5 via the port 6 and/or be retrieved from the chamber 5 via the port 6. For example, a needle biopsy can be introduced through port 6, which may include a re-sealing stopper, cap, or Luer lock. In certain embodiments, an analytical and/or preservative medium can be introduced into the chamber 5, and/or retrieved from the chamber 5, via the port 6. A plug 10 may be removably inserted into port 6 thereby sealing the chamber.

The second side 2B opposing the first side 2A defines an opening 7 communicating directly from the exterior of the container into the chamber 5. The opening 7 is configured to receive, or couple to, a closure element 8. In certain embodiments, the opening 7 and the closure element 8 are rectangular. In certain embodiments, the closure element 8 may be a removable cap or a Luer lock, with or without stop cocks. In certain embodiments, the closure element 8 may be a filter. In certain embodiments, a ridge 11 may be provided along the periphery of opening 7 and the closure element 8 is coupled to the container via contact with the ridge 11. In certain embodiments, the closure element 8 is impermeable. In other embodiments, the closure element 8 is perforated with at least one hole 9, preferably a plurality, of holes 9. In certain embodiments, a tissue specimen can be introduced into the chamber 5 via the hole(s) 9, for example, with a biopsy needle. In certain embodiments, an analytical and/or preservative medium may be introduced into the chamber 5 via the hole(s) 9. The holes 9 are aligned with the opening 8 so that they communicate directly from the exterior of the container into the chamber 5. A cover 12 (e.g, a plastic film or adhesive tape), which may or may not be removable, may be positioned a rigid surface made of holes of size less than 0.2 mm, or a filter-type surface (tea bag-like) that is flexible, and has holes less than 0.1 mm. The cover 12 should seal the hole(s) 9 so as to leak proof the chamber 5.

At least one specimen may be introduced into the chamber via the specimen port 6, the opening 7, and/or the hole(s) 9. In certain embodiments, the tissue specimen may be immobilized within the container so that it remains unperturbed such as by contact with the inner surfaces of the sides 2 and/or panels 3,4. In certain embodiments, the tissue specimen contacts and is supported by an inner surface of at least one the panels 3,4.

In certain embodiments, the specimen may be a tissue specimen introduced into the chamber 5 via a biopsy needle, particularly a core biopsy needle. For example, the container can receive a specimen obtained by a biopsy gun, a manual biopsy, or computer tomography-guided transvascular or transcutaneous sampling (e.g., via ultrasound, PET, MRI or fluoroscopy). The container can be used to receive a specimen from a fine needle aspiration biopsy. Once the biopsy needle is positioned within the chamber, the tissue specimen is ejected from the biopsy needle thereby introducing the tissue specimen into the chamber.

Figure 3:
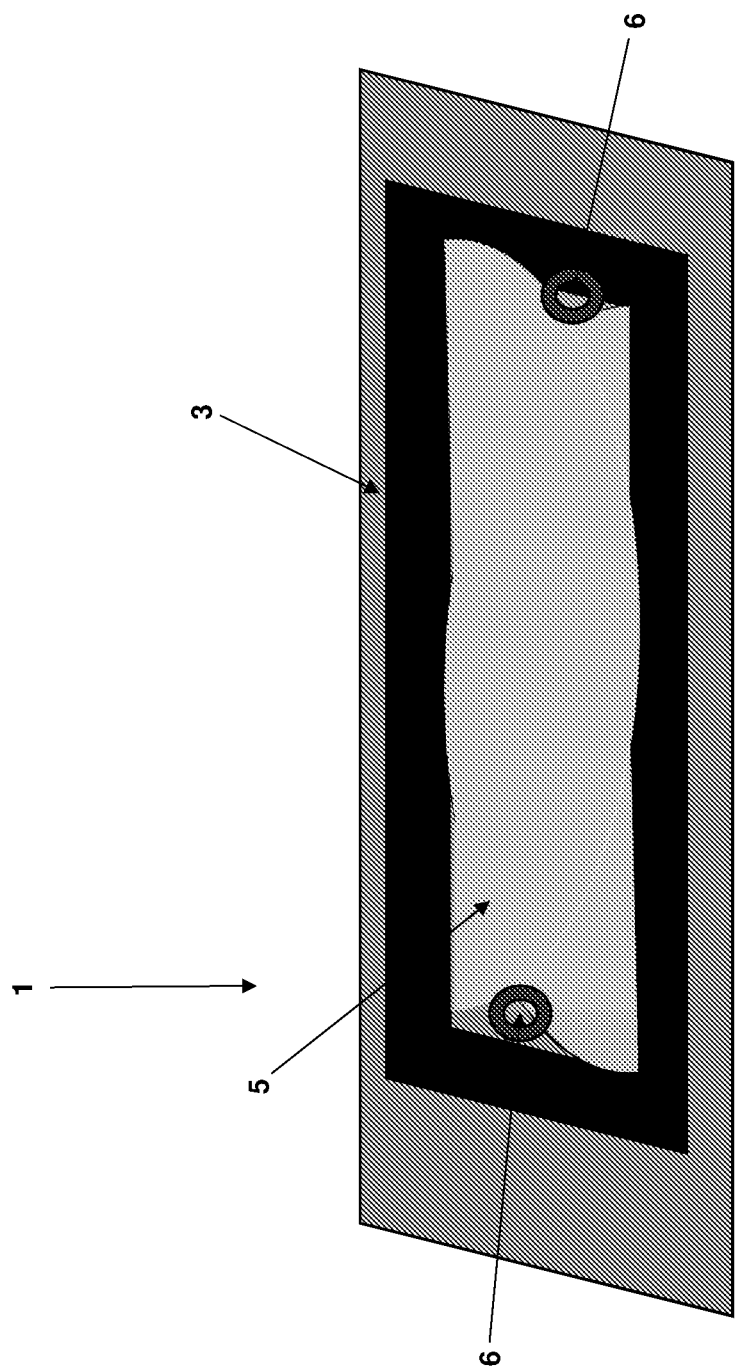
FIG. 3 is a schematic representation of a further embodiment of a container.
Figure 4A:
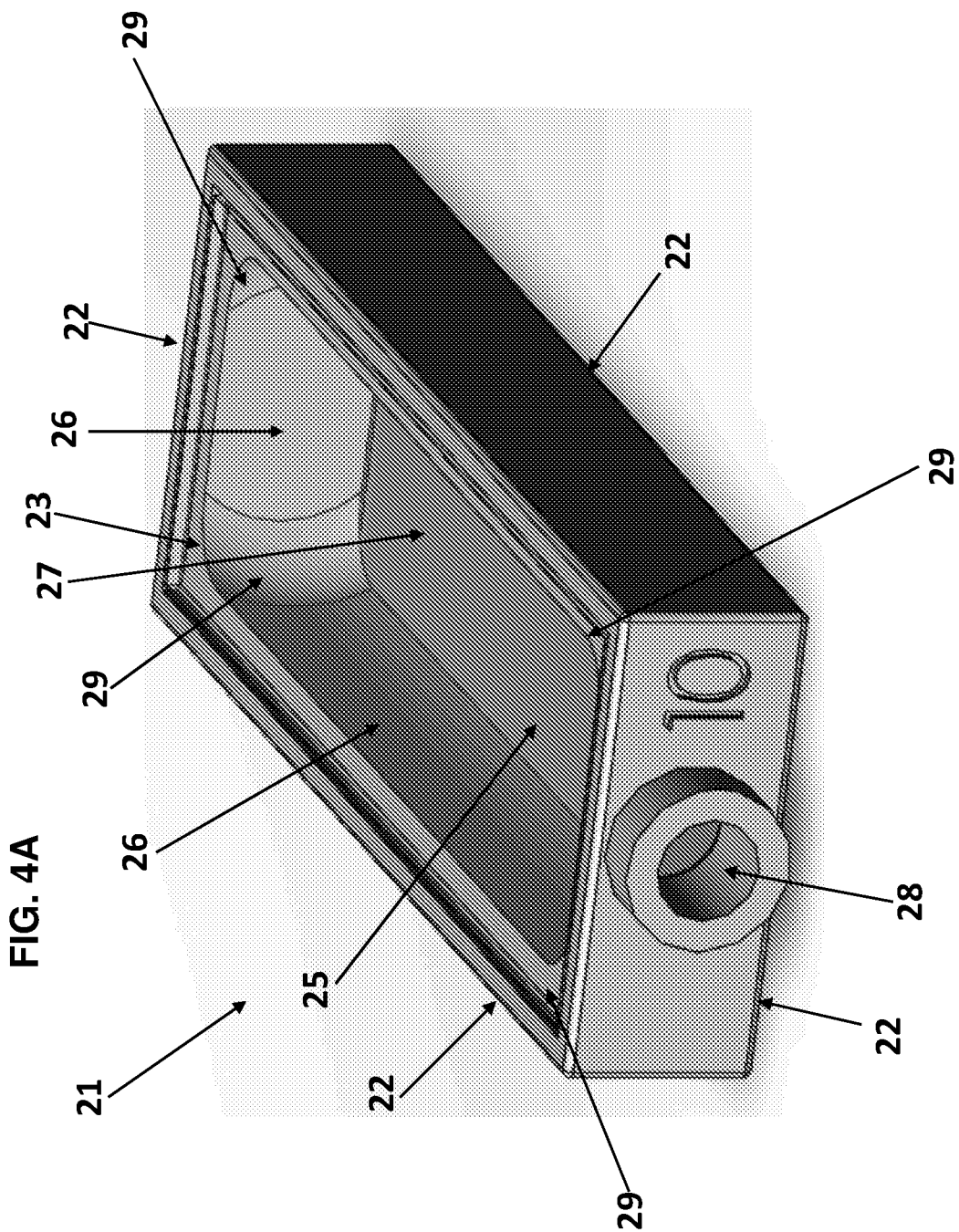
Figure 4B:
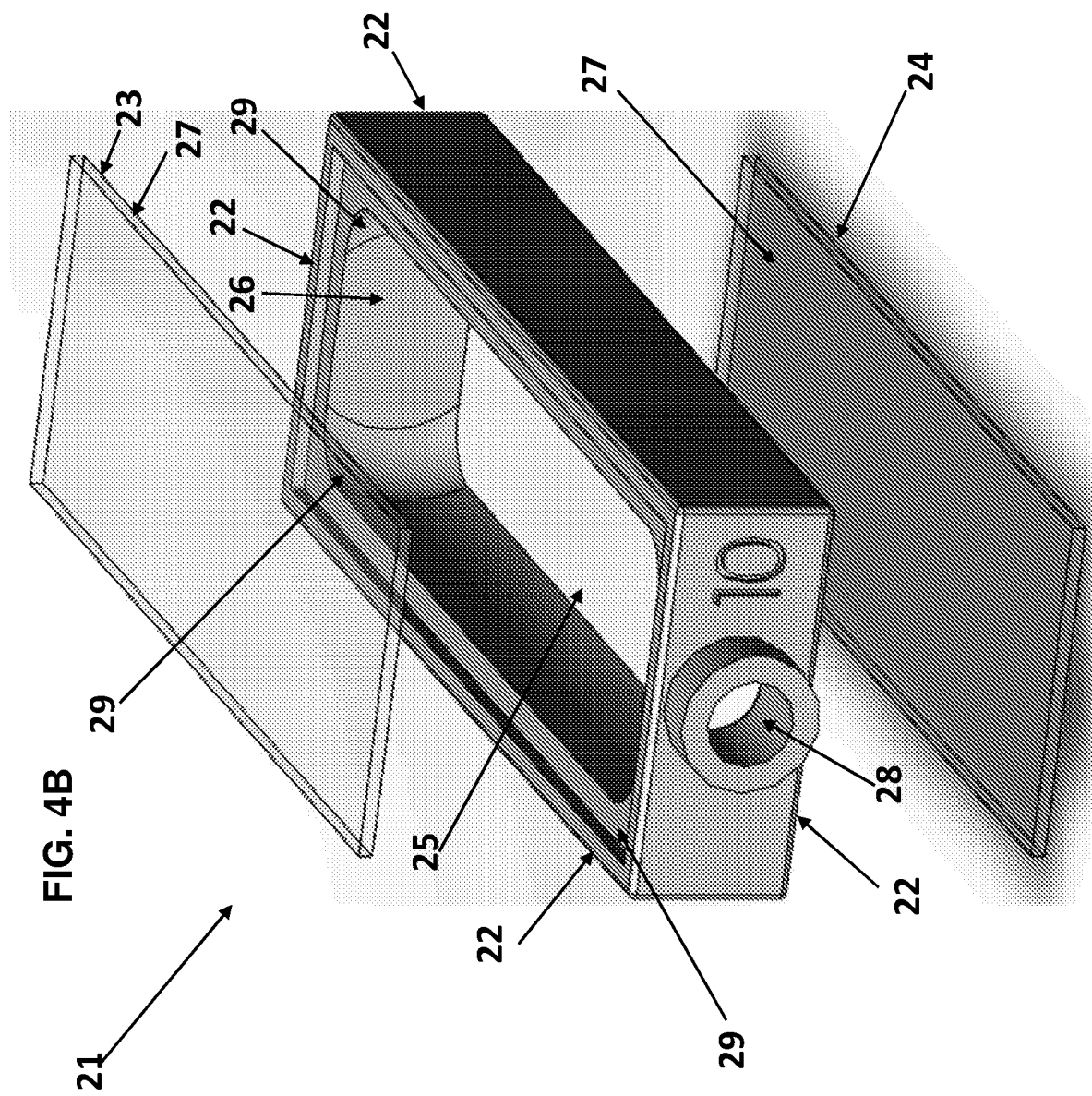

The container in FIG. 3 includes a rigid base, a chamber for receiving a specimen, and two ports for injection and withdrawal of the specimen and/or fluid. The container can be opened by pealing back a closure envelope.

FIGS. 4A-4D are views of another embodiment of a container 21 that includes a chamber 25 bounded by a curvilinear surface. The container 21 includes four sides 22, each of which joins a first panel 23 and a second panel 24. In certain embodiments, the four sides 22 together form a housing onto which the first and second panels 23,24 may be coupled. In certain embodiments, the first and second panels 23,24 may be removably coupled to the housing. At least one of the first or second panels 23,24 may be at least partially transparent. In the embodiment shown in FIGS. 4A-4D both first panel 23 and second panel 24 are entirely made from a transparent material (e.g., glass or plastic). The sides 22, first panel 23 and second panel 24 define an interior chamber 25. As described above, the chamber 25 is configured for receiving and retaining a specimen. Chamber 25 is defined by four peripheral side wall surfaces 26 and two peripheral panel surfaces 27. The two peripheral panel surfaces 27 are planar. The four peripheral side wall surfaces 26 are also the interior facing surfaces of the four sides 22, respectively. The two peripheral panel surfaces 27 are also the interior facing surfaces of the first panel 23 and second panel 24, respectively. The chamber 25 is rounded rectangular in shape that includes four rounded corner wall surfaces 29. The rounded corner wall surfaces 29 minimize the possibility that a sample or other material becomes stuck in a corner.

One of the sides 22 defines an opening 28 communicating directly from the exterior of the container into the interior chamber 25. In certain embodiments, a specimen can be introduced into chamber 25 via the opening 28 and/or be retrieved from the chamber 25 via the opening 28. In certain embodiments, a medium can also be introduced into the chamber 25, and/or retrieved from the chamber 25, via the opening 28. The embodiment shown in FIGS. 4A-4D may include more than opening. A plug or closure element as described above may also be associated with the opening(s) in the embodiment shown in FIGS. 4A-4D.

Figure 5B:
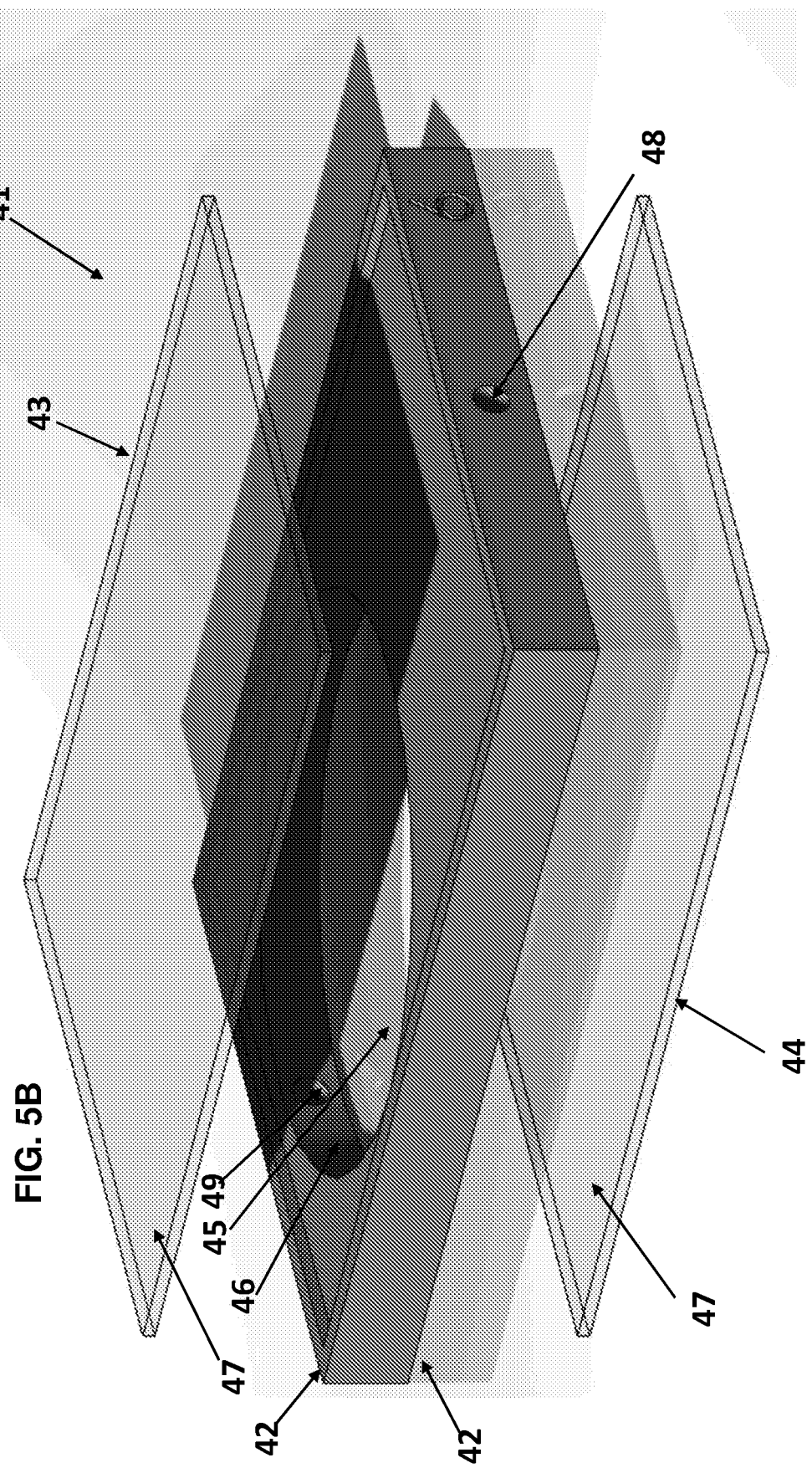

FIGS. 5A and 5B are views of a further embodiment of a container 41 that includes a chamber 45 bounded by a curvilinear surface. The container 41 includes four sides 42, each of which joins a first panel 43 and a second panel 44. In certain embodiments, the four sides 42 together form a housing onto which the first and second panels 43,44 may be coupled. In certain embodiments, the first and second panels 43,44 may be removably coupled to the housing. At least one of the first or second panels 43,44 may be at least partially transparent. In the embodiment shown in FIGS. 5A and 5B both first panel 43 and second panel 44 are entirely made from a transparent material (e.g., glass or plastic). The sides 42, first panel 43 and second panel 44 define an interior chamber 45. As described above, the chamber 45 is configured for receiving and retaining a specimen. Chamber 45 is defined by a peripheral side wall surface 46 and two peripheral panel surfaces 47. The two peripheral panel surfaces 47 are planar, and are also the interior facing surfaces of the first panel 43 and second panel 44, respectively. The peripheral side wall surface 46 defining the chamber 45 is curved. In the embodiment shown in FIGS. 5A and 5B the peripheral side wall surface 46 is in the shape of a circle when viewed from the top cross-section. Thus, the chamber 45 has a three-dimensional shape of a disc.

One of the sides 42 defines a first opening 48 communicating directly from the exterior of the container into the interior chamber 45. An opposing side 42 defines a second opening 48 communicating directly from the exterior of the container into the interior chamber 45. In certain embodiments, a specimen can be introduced into chamber 45 via the opening 48 or 49 and/or be retrieved from the chamber 45 via the opening 48 or 49. In certain embodiments, a medium can also be introduced into the chamber 45, and/or retrieved from the chamber 45, via the opening 48 or 49. A plug or closure element as described above may also be associated with the opening(s) in the embodiment shown in FIGS. 5A and 5B.

The embodiment shown in FIGS. 5A and 5B can accommodate larger format microscope slides (e.g, 50 mm×75 mm) as one or both of the panels 43,44. This design allows for a thinner chamber with increased volume for a medium. The chamber is also defined by circular wall surface to minimize the possibility that a sample or other material becomes stuck on the chamber wall.

An additional embodiment is shown in FIG. 6. A container 61 includes a first side end 62 and an opposing second side end 63. The container 61 also includes four elongated panels 64A-D, each of which joins the first side end 62 and the second side end 63. The panels 64A-D are more elongated relative to first side end 62 and second side end 63. A first pair of elongated panels 64A and 64B oppose each other. A second pair of elongated panels 64C and 64D oppose each other. The first end 62, the second end 63, and the four elongated panels 64A-D are all coupled to a housing 68. The housing 68 is in the form of an elongated frame defining voids that correspond to the respective locations of the first end 62, the second end 63, and the four elongated panels 64A-D. In the embodiment shown in FIG. 6 the housing 68 includes recessed lips or flanges 69 that can respectively receive the first end 62, the second end 63, and the four elongated panels 64A-D.

In certain embodiments, at least one of the first end 62, the second end 63, and the four elongated panels 64A-D are removably coupled to the housing 68. In certain embodiments, each of the first end 62, the second end 63, and the four elongated panels 64A-D are removably coupled to the housing 68.

In certain embodiments, at least one of the first end 62, the second end 63, and the four elongated panels 64A-D are at least partially transparent. In the embodiment shown in FIG. 6 all of the four elongated panels 64A-D are entirely made from a transparent material (e.g., glass or plastic).

The first end 62, the second end 63, and the four elongated panels 64A-D define an interior chamber 65. As described above, the chamber 65 is configured for receiving and retaining a specimen. Chamber 65 is defined by two peripheral side end wall surfaces 66 and four peripheral elongated panel surfaces 67. Each surface 66,67 is planar. The two peripheral side wall surfaces 66 are also the interior facing surfaces of the two side ends 62,63, respectively. The four peripheral elongated panel surfaces 67 are also the interior facing surfaces of the elongated panels 64A-D, respectively. The chamber 65 is rectangular (i.e., a cuboid) in shape, but could be other shapes such as a square.

Each of the first side end 62 and the second side end 63 is removable and thus can function as a cap for an opening communicating directly from the exterior of the container into the chamber 65. In certain embodiments, the first side end 62 and/or the second side end 63 can be removed thus allowing for introducing a specimen and/or medium into the chamber 65.

The container may be made with any suitable materials. For instance, the materials may be able to withstand extreme temperatures, pH, motion (i.e., shaking), and/or pressure changes.

In certain embodiments, the container enables immediate stabilization and transportation of needle biopsy tissue specimens by providing for depositing of the tissue directly into the chamber in the presence of a pre-defined desired solution and or a desired gas. The chamber may be pre-loaded with a tissue fixative in a controlled environment for killing the tissue rapidly (e.g. no warm ischemia time). The chamber may be pre-loaded with cell culture media to keep the specimen alive, bacteria culture media for microbiology investigation as required, or aerobic and anaerobic culture as suitable for microbiome studies. The fixatives or other solutions for culture could contain additional reagents to mediate staining of the cells. Examples include eosin (make the tissue visible), DAPI (label nuclei) or even an antibody which would be used for the selection of cells in the container unit (or outside) including by the addition of iron on the ab (magnetic selection), or an enzyme to mediate disassociation of tissue (collagenase or other protease) to generate a cell suspension (allowing selection of specific cell types).

The needle biopsy tissue specimen may be directly deposited (i.e, "directly" means that the specimen is not introduced or deposited into another apparatus between the biopsy procedure and depositing into the here-described container) into the chamber via any opening such as a port, a lid or a removed side. Larger biopsies such punch biopsies may be introduced into the chamber via a lid or a removed side.

The container chamber may be used for a collection of cells from effusions, ascites, saliva, or urine. For example, cells may be: collected, fixed in the chamber and removed; collected and injected into a medium in the chamber to grow; or injected into a gel in the chamber for staining and imaging. In a further example, the cells may be placed in the chamber, the container unit then placed in a swinging bucket centrifuge (using an adaptor to a 96 well plate) with a glass slide of the container down and spun such that the cells in the solution are adhered via centrifugation to the glass side. The slide may be removed from the container and examined. The cells could be fixed in the container prior to, or after, centrifuging. The cells could be stained prior to, or after, centrifuging. In another example, the cells may be presented on the interior surface (i.e., one of the chamber surfaces) of a transparent, optionally removable, side or panel of the container. In certain embodiments, the cells may be from in vitro experiments such as tissue from animals, xenograft samples, and patient-derived xenograft samples.

In certain embodiments, the tissue sample is maintained in a sterile environment within the chamber for at least 12 hours, more particularly at least 72 hours, such that tissue cell viability (e.g., at least 80% of the cells are alive) and morphology (e.g., cells do not look any different when compared to the freshly collected sample) is maintained.

A tissue sample or cellular aspirate obtained by needle biopsy may be directly and immediately placed in the chamber, visualized at the site of collection, and then transported to a clinical laboratory for removal of the tissue for downstream analysis. The environment is sterile and the container is suitable for visualization under a microscope for inspection of the specimen (e.g., to assess quality, quantity, and pathology). The rapid introduction into a controlled environment provided in the chamber limits degradation of the specimen. Additional optional features include features to detect specimen damage from handling and transportation, and detection of pathological states (fibrosis, malignancy, infection).

The container has application for: tissue biopsies for medical disorders (such as the liver and kidney), cancer biopsies for the assessment of the presence of tumor, bacteria and/or response to treatment, including diagnosis, prognosis and predictive medicine evaluation of transplant tissue (kidney, liver, heart, lungs, pancreas), evaluation of the immune system, and/or tumor-immune system interactions (tumor, lymph node), metabolic disorders (fat), organ injury or repair or microbiome (any organ), research applications for preservation of DNA, RNA, protein or lipids as well as viable cells, and biosafety applications. Material obtained by aspiration could also be placed in the container.

In certain embodiments, the container can collect tissue exposed to infectious agents such that the chamber and tissue within the chamber (with or without the fixative) can be autoclaved and the tissue can then be removed for histologic and molecular evaluation in a BSL3, BSL3+ or BSL4 laboratory.

In certain embodiments, the container allows for transporting of tissue, cell, bacteria and liquid samples for the evaluation and diagnosis (as well as prognosis and predictive/precision medicine) of, but not limited to: cancer, infection (viral, bacterial, fungal), autoimmune disorders, metabolic disorders, genetic disorders, or uncharacterized/investigative conditions.

The container may be utilized with any tissue specimen, including, but not limited to: lung, liver, kidney, breast, bone marrow, lymph node, prostate, thyroid, pancreas, salivary gland, etc. The container can be used for human specimens as well as animal tissue (food stock and wild animals) for research or clinical use. The container can also be used for collecting soil or plant material.

The sample in the container may be observed Observation under a microscope, light-sheet microscope (4-side glass units), by means of "structured illumination" including LED, LASER, UV, as well as different types of light bulbs with: Upright, Inverted microscopes, as well as stereoscopes and rack-mounted magnification devices.

In certain embodiments, the container may be included in a system that includes a stand that would stabilize the container while introducing a sample. For example, the stand may include a slot or a similar type of recess for holding the container at a 25° to 75° angle relative to a horizontal surface thereby facilitating insertion of a biopsy needle into the chamber.

An illustrative holder 80 for a container 83 is shown in FIG. 7. The holder 80 includes a first base section 81 and second base section 82. The first base section 81 and the second base section 82 are coupled to each other at the respective centers of each section 81, 82 so as to define a slot 84 for receiving the container 83. In the embodiment shown in FIG. 7 the first base section 81 and the second base section 82 intersect at a 90° angle. An optional guide section 85 is secured above the slot 84. A funnel 86 (or similar specimen and/or medium introduction element) positioned above the slot 84 communicates with an opening 87 in the container 83 for introducing a specimen and/or medium. The funnel 86 may be retained by guide section 85. The container 83 is placed into the slot 84, and then a specimen and/or medium is introduced into the chamber of the container.

Several embodiments are described below in the following numbered clauses:

1. A container comprising:
a first panel;
a second panel opposing the first panel;
a first side;
a second side opposing the first side;
a third side;
a fourth side opposing the third side;
wherein each of the sides joins the first panel and the second panel;
a chamber defined by the four sides, the first panel, and the second panel, wherein the chamber is configured to receive a biological specimen;
a port defined in the first side;
a plug inserted into the port;
an opening defined in the second side; and
a closure element coupled to the opening,
wherein the chamber is leak proof.

2. The container of clause 1, wherein at least one of the first panel or the second panel is transparent.

3. The container of clause 1 or 2, wherein both the first panel and the second panel are transparent.

4. The container of any one of clauses 1 to 3, wherein the closure element is perforated with at least one hole that communicates with the opening in the second side.

5. The container of any one of clauses 1 to 4, wherein the closure element is removably coupled to the opening of the second side.

6. The container of any one of clauses 1 to 5, wherein the container is in the shape of a rectangular cuboid.

7. The container of any one of clauses 1 to 6, wherein the second side includes a ridge aligned along the periphery of the opening, and the closure element is a cap removably coupled to the ridge.

8. The container of any one of clauses 1 to 7, wherein the port is circular and the opening is rectangular.

9. The container of any one of clauses 1 to 8, wherein a medium resides within the chamber.

10. A container in the shape of a rectangular cuboid comprising:
a transparent first panel;
a transparent second panel opposing the first panel;
a first side;
a second side opposing the first side;
a third side;
a fourth side opposing the third side;
wherein each of the sides joins the first panel and the second panel;
a chamber defined by the four sides, the first panel, and the second panel, wherein the chamber is configured to receive a biological specimen;
a port defined in the first side;
an opening defined in the second side; and
a closure element coupled to the opening, wherein the closure element is perforated with at least one hole that communicates with the opening in the second side.

11. The container of clause 10, wherein the second side includes a ridge aligned along the periphery of the opening, and the closure element is a cap removably coupled to the ridge.

12. The container of clause 10 or 11, wherein the port is circular and the opening is rectangular.

13. The container of any one of clauses 10 to 12, wherein a medium resides within the chamber.

14. A method for collecting and storing a biological specimen, comprising obtaining a biological specimen from a subject and placing the biological specimen in the chamber of a container of any one clauses 1 to 13.

15. A method for collecting and storing a tissue sample, comprising obtaining a tissue sample from a subject via biopsy needle and inserting the tissue sample-loaded biopsy needle into the chamber of a container of any one of clauses 1 to 13 via the closure element.

16. The method of clause 14, wherein the tissue sample is maintained in a sterile environment within the chamber for at least 12 hours such that tissue cell viability and morphology is maintained.

In view of the many possible embodiments to which the principles of the disclosed invention may be applied, it should be recognized that the illustrated embodiments are only preferred examples and should not be taken as limiting the scope of the invention.

What is claimed is:

1. A container comprising:
   a first panel;
   a second panel opposing the first panel;
   a first side;
   a second side opposing the first side;
   a third side;
   a fourth side opposing the third side;
   wherein each of the sides joins the first panel and the second panel;
   a chamber defined by the four sides, the first panel, and the second panel, wherein the chamber is configured to receive a biological specimen;
   a port defined in the first side;
   a first closure element coupled to the port;
   an opening defined in the second side; and
   a second closure element coupled to the opening, wherein the second closure element is perforated with a plurality of holes that communicate with the opening in the second side,
   wherein a medium resides within the chamber, the medium selected from a tissue culture medium; a tissue culture fixative; nitrogen gas; argon gas; carbon monoxide gas; a sulfur-containing gas; oxygen gas; xenon gas; carbon dioxide gas; neutral buffered formaldehyde; water; saline; cell culture media; an alcohol; glycerol; mineral oil; proteolytic inhibitors; RNA degradation inhibitors; glycol; acid; argon-enriched atmosphere in contact with Formalin-Fixation Paraffin Embedding (FFPE); a fixative comprising ethanol, a buffer, glycerol, and acetic acid; an enzyme to mediate disassociation of tissue; or a combination thereof.

2. The container of claim 1, wherein at least one of the first panel or the second panel is optically transparent.

3. The container of claim 1, wherein both the first panel and the second panel are optically transparent.

4. The container of claim 1, wherein the second closure element is removably coupled to the opening of the second side.

5. The container of claim 1, wherein the container is in the shape of a rectangular cuboid.

6. The container of claim 1, wherein the second side includes a ridge aligned along the periphery of the opening, and the second closure element is a cap removably coupled to the ridge.

7. The container of claim 1, wherein the port is circular and the opening is rectangular.

8. The container of claim 1, wherein the chamber includes rounded corner walls.

9. The container of claim 1, wherein the chamber has a curvilinear peripheral wall.

10. A container in the shape of a rectangular cuboid comprising:
    a optically transparent first panel;
    a optically transparent second panel opposing the first panel;
    a first side;
    a second side opposing the first side;
    a third side;
    a fourth side opposing the third side;
    wherein each of the sides joins the first panel and the second panel;
    a chamber defined by the four sides, the first panel, and the second panel, wherein the chamber is configured to receive a biological specimen;
    a port defined in the first side;
    an opening defined in the second side; and
    a closure element coupled to the opening, wherein the closure element is perforated with a plurality of holes that communicate with the opening in the second side.

11. The container of claim 10, wherein the second side includes a ridge aligned along the periphery of the opening, and the closure element is a cap removably coupled to the ridge.

12. The container of claim 10, wherein the port is circular and the opening is rectangular.

13. The container of claim 10, wherein the chamber includes rounded corner walls.

14. The container of claim 10, wherein the chamber has a curvilinear peripheral wall.

15. A container comprising:
    a first panel;
    a second panel opposing the first panel;
    a first side;
    a second side opposing the first side;
    a third side;
    a fourth side opposing the third side;
    wherein each of the sides joins the first panel and the second panel;
    an internal disc-shaped chamber defined by a peripheral side wall and two opposing planar surfaces, wherein the peripheral side wall of the chamber is curvilinear; and
    at least one opening in at least one of the first panel, the second panel, the first side, the second side, the third side or the fourth side, wherein the opening communicates from exterior of the container into the chamber and wherein the opening is configured to introduce a biological specimen into the chamber.

16. The container of claim 15, wherein the peripheral side wall of the chamber has a rounded rectangle shape.

17. The container of claim 15, wherein the peripheral side wall of the chamber includes rounded corner walls.

18. The container of claim 15, wherein a medium resides within the chamber.

19. A container comprising:
    a transparent elongated first panel having an exterior surface and an interior surface;
    a transparent elongated second panel opposing the first panel, wherein the second panel has an exterior surface and an interior surface;
    a transparent elongated third panel having an exterior surface and an interior surface;
    a transparent elongated fourth panel opposing the third panel, wherein the second panel has an exterior surface and an interior surface;
    a first end having an exterior surface and an interior surface;

a second end opposing the first end, the second end having an exterior surface and an interior surface, wherein at least one of the first end and the second end is removable;

a housing coupled to, and supporting, the first panel, the second panel, the third panel, the fourth panel, the first end, and the second end, wherein the housing comprises a frame that has voids that respectively receive the first panel, the second panel, the third panel, the fourth panel, the first end, and the second end, and at least one of the first panel, the second panel, the third panel, the fourth panel, the first end, or the second end, is detachably coupled to the housing; and an internal chamber bounded by the interior surface of the first panel, the interior surface of the second panel, the interior surface of the third panel, the interior surface of the fourth panel, the interior surface of the first end, and the interior surface of the second end.

20. The container of claim 19, wherein a medium resides within the chamber.

21. A method for collecting and storing a biological specimen, comprising obtaining a biological specimen from a subject and placing the biological specimen in the chamber of a container of claim 1.

22. A method for collecting and storing a tissue sample, comprising obtaining a tissue sample from a subject via biopsy needle and inserting the tissue sample-loaded biopsy needle into the chamber of a container of claim 1 via the closure element.

23. The method of claim 22, wherein the tissue sample is maintained in a sterile environment within the chamber for at least 12 hours such that tissue cell viability and morphology is maintained.

24. The container of claim 1, wherein the container has a length of 4 cm to 8 cm, and a width of 2.5 cm to 5 cm.

25. The container of claim 1, wherein the first closure element comprises a luer lock.

26. The container of claim 1, wherein the second closure element comprises a luer lock.

27. The container of claim 10, wherein the optically transparent first panel or the optically transparent second panel comprises a slide glass, or each of the optically transparent first panel and the optically transparent second panel comprises a slide glass.

28. The container claim 10, wherein the optically transparent first panel or the optically transparent second panel comprises a coverslip glass, or each of the optically transparent first panel and the optically transparent second panel comprises a coverslip glass.

29. The container of claim 10, wherein the optically transparent first panel or the optically transparent second panel comprises a plastic material having a defined refractive index of 1.33 to 1.62, or each of the optically transparent first panel and the optically transparent second panel comprises a plastic material having a defined refractive index of 1.33 to 1.62.

30. The container of claim 10, wherein each of the first side, the second side, the third side and the fourth side are optically transparent.

31. The container of claim 19, wherein each of the first panel, the second panel, the third panel, the fourth panel, the first end, and the second end is detachably coupled to the housing.

32. A device for holding the container of claim 1, wherein the device comprises a first base section and a second base section, wherein the first base section and the second base section are coupled together and intersect at a 90° angle so as to form a slot for receiving the container.

33. A device for holding the container of claim 10, wherein the device comprises a first base section and a second base section, wherein the first base section and the second base section are coupled together and intersect at a 90° angle so as to form a slot for receiving the container.

* * * * *